United States Patent [19]

Sundkvist et al.

[11] 4,276,777
[45] Jul. 7, 1981

[54] APPARATUS FOR ANALYSING FLOWING MEDIA

[75] Inventors: Gustaf J. Sundkvist, Skelleftehamn; Fred O. Lundgren, Skellefteå; Mats-Ove R. Lindberg, Skelleftehamn; Erik A. Boström, Skellefteå, all of Sweden

[73] Assignee: Boliden Aktiebolag, Stockholm, Sweden

[21] Appl. No.: 174,526

[22] PCT Filed: Dec. 6, 1979

[86] PCT No.: PCT/SE79/00088

§ 371 Date: Dec. 6, 1979

§ 102(e) Date: Dec. 6, 1979

[87] PCT Pub. No.: WO79/00934

PCT Pub. Date: Nov. 15, 1979

[30] Foreign Application Priority Data

Apr. 14, 1978 [SE] Sweden .................. 7804262

[51] Int. Cl.³ .................. G01N 1/10; G01N 23/00
[52] U.S. Cl. .................. 73/864.81; 250/434
[58] Field of Search .................. 73/421 R; 23/230 R, 23/230 A; 250/573, 575, 576, 432 R, 434, 435; 356/440, 244

[56] References Cited

U.S. PATENT DOCUMENTS 3,121,789  2/1964  McGrath .................. 250/432 R
3,744,974  7/1973  Maddox et al. .................. 250/576 X

FOREIGN PATENT DOCUMENTS 1673254  9/1971  Fed. Rep. of Germany .
 503274  3/1971  Switzerland .
 303573  5/1972  U.S.S.R. .................. 250/432

*Primary Examiner*—James J. Gill
*Attorney, Agent, or Firm*—Stevens, Davis, Miller & Mosher

[57] ABSTRACT

An apparatus for use in the analysis of flowing media, and in particular for the analysis of pulp-flows taken from different locations in at least one flotation plant is illustrated in FIG. 1. The apparatus comprises analysis cells (22) through each of which a respective one of said media is caused to flow. The cells are arranged to be brought one at a time into a respective position for co-operation with an analysis instrument (20), by a movable carrying means. The movable carrier means (21) is rotatable about a substantially vertical axis (24) and carries the cells (22) adjacent to one another along a substantially horizontal circular-arcuate line which has its center on said axis. The movable carrying means are made of an elastomeric material. Further, to maintain satisfactory through-flow conditions, the lines are joined to form a collected bunch (49) of lines comprising substantially vertically extending line-sections, said bunch being arranged concentrically relative to said axis, and from which bunch said lines extend obliquely downwardly and outwardly to respective associated analysis cells (22).

4 Claims, 3 Drawing Figures

APPARATUS FOR ANALYSING FLOWING MEDIA

The present invention relates to an apparatus for use in the analysis of flowing media, and in particular for the analysis of pulp-flows taken from different locations in at least one flotation plant, in which apparatus analysis cells, through each of which a respective one of said media flows, are brought one at a time into a respective position for co-operation with an analysis instrument, particularly an X-ray analyser, which apparatus includes supply lines by which the analysis cells can be connected to associated media sources; a stationary means for carrying said instrument; a movable means for carrying said cells; means for setting the movable carrying means relative to the stationary carrying means such that the cells are placed relative to the analysis instrument; and means for collecting the media departing from said cells.

Apparatus of the type described are now being used to an ever increasing extent for controlling concentrating processes, and in particular flotation processes. It is known in such apparatus to arrange the analysis cells adjacent one another in a straight, horizontal line and to index forwards either the cell-carrying means or the analysis-instrument carrying means in a direction parallel with said straight line, and to bring said analysis cells and the analysis instrument in a position for mutual co-operation therebetween. A relatively large space is required to effect this rectilinear movement of the two carrying means. Furthermore, movement of the analysis instrument, which often is a very delicate instrument, may lead to disturbances which result in an erroneous analysis result, whilst movement of the analysis cells necessitates the use of long, flexible supply lines for those media to be analysed. The lines supplying the analysis cells become distorted when the cell-carrying means is moved rectilinearly, which can also lead to an erroneous analysis result because of the change in flow conditions through the said cells occurring as a result thereof. The object of the present invention is to privide a novel and improved apparatus of the type mentioned in the introduction, in which the aforementioned disadvantages are eliminated at least to a substantial extent. To this end, it is proposed in accordance with the present invention that the movable carrier means is rotatable about a substantially vertical axis and carries the cells adjacent to one another along a substantially horizontal circular-arcuate line which is concentrical with said axis; and that in an area located at a distance above the level of said cells the supply lines extending from the sources of said media to said analysis cells comprise an elastomeric material and are joined to form a collected bunch of lines comprising substantially vertically extending line-sections and arranged concentrically relative to said axis, from which bunch said lines extend obliquely downwardly and outwardly to respective associated analysis cells. Through this arrangement, the movement required to set the position of the movable carrying means will only result in very slight bending and twisting of the elastomeric sections of the supply lines, thereby to ensure uniform flow conditions whilst saving a considerable amount of space.

When each of the aforementioned analysis cells is connected to a separate discharge line, the discharge lines, in accordance with a further development of the invention, can extend obliquely downwardly and inwardly and may comprise an elastomeric material in a region located at a distance beneath the level of the analysis cells, and, similarly to the supply lines, may be collected into a bunch which is concentrical with said axis.

For the purpose of collecting the said supply and discharge lines into said bunch or bunches, said lines can be passed through a rotatable sleeve which may be stationary or arranged for movement together with said movable carrying means, whereby said sleeve may be provided with an insert by which the lines are prevented from clamping against each other, said insert being conveniently provided with a respective through-passing hole for each of said lines.

In order to make the invention more readily understood and optional features thereof made apparent, an exemplary embodiment of the invention will now be described with reference to the accompanying schematic drawings, in which.

The apparatus illustrated in the Figures comprises a frame 10 having three legs, 11, 12, 13 mutually connected together by means of cross members 14–18. The leg 12 carries a plate 19 and forms a stationary carrying means for an analysis instrument, for example an X-ray analyser, shown in dash lines at 20.

Figure 1:
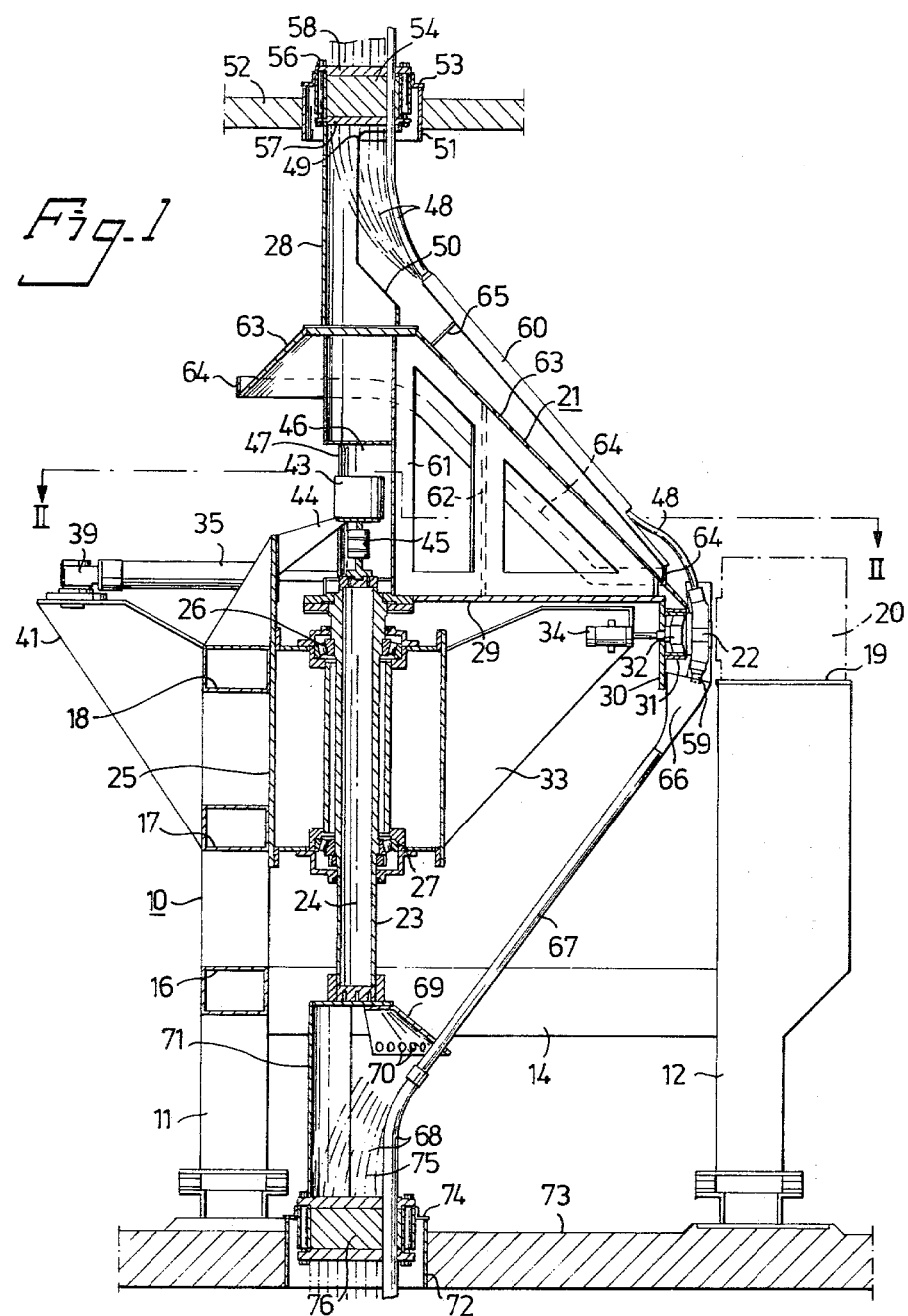
FIG. 1 is a view of an apparatus according to the invention taken substantially on the line I—I in FIG. 2.

The frame 10 also carries a movable carrying means, shown generally at 21, which carries a multiplicity of analysis cells, of which only one is shown at 22 in FIG. 1. The carrying means 21 includes a vertical, tubular part 23 which is carried for rotation about its vertical geometric axis 24 by frame parts 17 and 18 through a stationary bracket structure 25 and upper and lower bearings 26, 27 carried thereby. The tubular section 23 carries at its upper end a substantially tubular extension part 28 which is coaxial with the axis 24, and a horizontal plate 29 in the form of a sector of a circle and having a vertical, angled peripheral edge part 30. The edge part 30 extends along a horizontal circular-arcuate line whose center is located on the axis 24, and carries a multiplicity of uniformly spaced holders for the analysis cells 22, said holders being located on one and the same level. Only one of said holders, 31, is shown in FIG. 1.

In the illustrated embodiment, each holder 31 exhibits a horizontal sleeve-like part which accommodates a spring means 32, which when no load acts thereupon attempts to hold the analysis cell 22 out of contact with the instrument 20, but which, when a cell is located opposite said instrument, can be activated by means of the piston rod of a piston-cylinder arrangement 34 mounted on a part 33 of the bracket structure 25. To this end, the piston rod is arranged to pass into a bore extending through the edge part 30 opposite each holder 31.

Rotation of the movable carrying means 21 is effected by two piston-cylinder arrangements 35, 36, the outer ends of the piston rods of which are pivotally connected to the plate 29 at 37 and 38, whilst the opposite ends of the cylinders are each pivotally connected at 39 and 40 to a respective bracket structure 41 and 42 carried by the frame 10. For the purpose of controlling said rotation of the movable carrying means 21 by the pressure cylinders 35, 36, there is provided an indicator 43 which indicates the angle through which said carrying means 21 is rotated, said indicator being carried by a bracket 44 which in turn is carried by the frame 10. The input shaft of the indicator 43 is coaxial with the axis 24 and is connected to the upper end of the tubular section 23 via a coupling 45. The indicator 43 and the coupling 45 are accommodated in a space 46 in the tubular extension part 28. This space is provided at 47 with an opening of sufficient size to enable the requisite turning of the movable carrying means 21 relative to the part of the bracket 44 located in the opening 47.

Each analysis cell 22 comprises a tubular body, which is slightly flattened out in a direction at right angles to said edge part 30 and which has facing radially outwardly from said part 30 a window in the form of an opening covered with a thin, exchangeable plastics foil. When carrying out an analysis, this window is pressed into a given position relative to the instrument 20 by means of the piston-cylinder arrangement 34 acting against the cell through said spring means 32, said given position being determined by locating means (not shown) arranged on the analysis cell and the analysis instrument.

The analysis cells 22 are connected to various locations in, for example, a flotation plant (not shown) located above the apparatus illustrated in FIG. 1. Sample flows of flotation pulp to be analysed are passed, either continuously or intermittently, to the analysis cells 22 gravitationally through supply lines 48, of which one is illustrated in full lines in FIG. 1 whilst the remaining supply lines are shown in dash lines. The supply lines 48 are made of an elastomeric material and extend downwardly into and through the sleeve-like upper end of the extension part 28, in which they are held together in a collected bunch 49. The part 28 exhibits at 50 a lateral opening through which the lines 48 pass in a fan-like fashion obliquely downwardly and outwardly to the upper part of respective analysis cell 22. The part 28 extends up through an opening defined by a ring 51 in a ceiling structure 52 arranged at the top of the apparatus shown in FIG. 1, the gap between the ring 51 and the part 28 being sealed by means of an elastic collar 53. Arranged in the upper end of the sleeve-like part 28 is an insert 54 provided with through-passing holes 55 (FIG. 3) for receiving a respective one of said lines 48, said lines being held fixed in position by means of perforated end plates 57, 58 held together by bolts 56, of said plates 57, being fixedly connected to the extension part 28 and said plate 57 and the other, 58, being moveable in the direction of said axis 24 towards the insert 54. The sample flows depart from each of the analysis cells 22 through an outlet 59 formed from a short piece of rubber hose, the through-flow area of said outlet 59 being adjustable by means of a hose clamp (not referred), thereby to adjust the pressure within the analysis cell to a desired magnitude.

The parts of the supply lines 48 extending between the opening 50 and analysis cells 22 rest in guides 60 carried by a support structure which includes support elements 61, 62, arranged on the plate 29, and a substantially conical element 63 which is arranged above said support elements and which is arranged to protect the plate 29, the connecting locations 37, 38 of respective cylinders 35, 36 and the brackets 25, 44, should a supply line 48 fracture or rupture, said conical element 63 exhibiting a vertically upwardly bent edge portion 64, such that any flotation pulp which might leak out will be collected at the periphery of said conical element, from where it can be led away through an outlet not shown. The guides 60 are carried by the edge part 64 of the substantially conical element 63 and by support pegs 65 upstanding from said element.

The outlets 59 of analysis cells 22 each discharge into a respective funnel 66, from which sample-flows, which have passed through the analysis cells, can flow to collecting vessels (not shown), via pipes 67 and lines or hoses 68 of elastomeric material, and be pumped from said collecting vessels back to the flotation plant.

The funnels 66 are connected to the angled edge part 30 of the circle-sector-shaped plate 29, and the pipes 67 extend obliquely downwardly and inwardly to and through a holder 69 carried by the lower end of the tubular part 23, said holder having the form of a part of a conical element with holes 70 adjacent the base edge to receive said pipes 67. Also connecting with the lower end of the tubular part 23 is an extension part 71 having a sleeve-like end part which is accommodated in an opening in a floor structure 73 carrying the apparatus according to the invention, said opening being defined by a ring 72 and the gap between said ring and the sleeve-like end part being sealed by means of an elastic collar 74. The lines 68 comprising elastomeric material pass through the said sleeve-like end part and are held together thereby to form a collected, vertically extending bunch 75 of lines, said bunch being substantially concentrical with the axis 24. Similar to the manner described with reference to the bunch 49, there is arranged in the sleeve-like end part of the extension part 71, an insert 76 having a through-passing hole for each of the lines 68.

Figure 2:
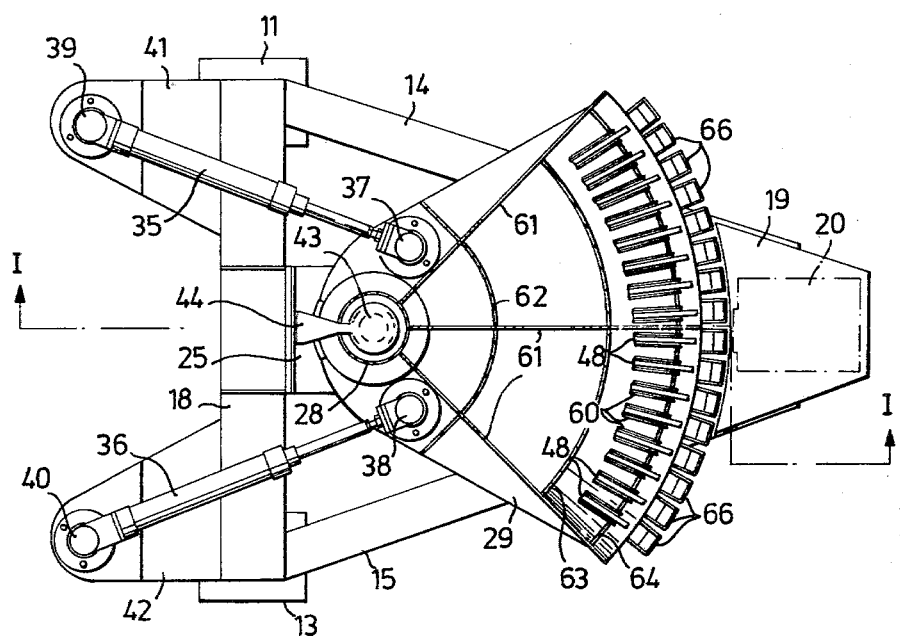
FIG. 2 is a view taken substantially on the line II—II in FIG. 1, certain elements being omitted in this view so that the features typical of the invention can be seen more clearly.
Figure 3:
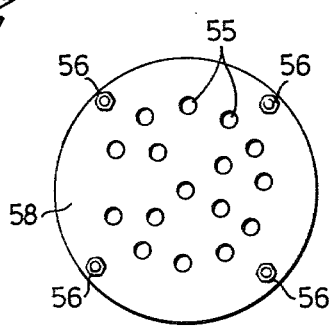
FIG. 3 is an end view of the uppermost sleeve construction shown in FIG. 1, said sleeve being intended to hold the supply lines together in bunch form.

When using the apparatus shown in FIGS. 1–3, the carrying means 21 is rotated stepwise by means of the cylinders 35, 36 in accordance with a desired pattern, to positions in which the analysis cells 22 are brought, one at a time, into respective positions for co-operating with the analysis instrument. This rotation of the carrying means can be controlled manually and/or through a programmed control means, which includes the aforementioned indicator 43. Subsequent to an analysis cell 22 having been placed in position opposite the analysis instrument, the analysis cell is urged against the instrument 20 for the purpose of finely setting said cell relative said instrument. It will be readily understood that the apparatus according to the invention will only take up a small amount of floor space, as a result of the rotatability of the carrying means 21 and as a result of the fact that the elastomeric supply and discharge lines 48, 68 are collected to form bunches 49, 75 which are concentrical with the axis of rotation 24, and that the shape of the lines 48, 68 will only be changed very slightly by said rotation, such that the flow conditions for the media passing through said lines remains substantially unchanged. As explained in the introduction, this latter feature is of particular importance when a high degree of accuracy is desired in the analysis of the media passing through the lines 48.

The invention is not restricted to the illustrated and aforedescribed embodiment and field of application, but can be modified within the scope of the following claims. The term analysis as used here shall be widely interpreted and shall include a pure flow-measuring process and a quantitative and qualitative analysis of the media-flows passing through the analysis cells or of certain components of said flows.

We claim:

1. An apparatus for use in the analysis of flowing media, and in particular for the analysis of pulp-flows taken from different locations in at least one flotation plant, in which apparatus analysis cells (22) through each of which a respective one of said media flows, are brought one at a time into a respective position for co-operation with an analysis instrument (20), particularly an X-ray analyser, which includes supply lines (48) by which the analysis cells can be connected to associated media sources; a stationary means (12, 19) for carrying said instrument; a movable means (21) for carrying said cells (22); means (35, 36) for setting the movable carrying means relative to the stationary means such that the cells are placed relative to the analysis instrument; and means (66, 67, 68) for collecting the media departing from said cells, characterized in that the movable carrier means (21) is rotatable about a substantially vertical axis (24) and carries the cells (22) adjacent to one another along a substantially horizontal circular-arcuate line which is concentrical with said axis; and that in an area located at a distance above the level of said cells the supply lines (48) extending from the sources of said media to said analysis cells comprise an elastomeric material and are joined to form a collected bunch (49) of lines comprising substantially vertically extending line-sections and arranged concentrically relative to said axis, from which bunch said lines extend obliquely downwardly and outwardly to respective associated analysis cells (22).

2. An apparatus according to claim 1, characterized in that each of the analysis cells (22) is connected to a respective discharge line (66, 67, 68), said discharge lines extending obliquely downwardly and inwardly and comprise in an area located at a distance beneath the level of the analysis cells an elastomeric material and are, similar to the supply lines (48), collected to form a bunch (75) which is concentrical with said axis (24).

3. An apparatus according to claim 1 or 2, characterized in that for the purpose of forming said bunch or bunches (49, 75) the supply and/or the discharge lines (48, 66, 67, 68) extend through a rotatable sleeve which may be stationary or arranged for rotation together with the carrier means (21).

4. An apparatus according to claim 3, characterized by an insert (54, 76) arranged in said sleeve, said insert being provided with through-passing holes arranged to accommodate a respective one of said lines (48, 66, 67, 68).

* * * * *